(12) United States Patent
Kobayashi

(10) Patent No.: US 6,780,812 B2
(45) Date of Patent: Aug. 24, 2004

(54) CHIRAL LEAD CATALYST AND METHOD OF ASYMMETRIC ALDOL REACTION

(75) Inventor: Shu Kobayashi, Saitama (JP)

(73) Assignee: Japan Science and Technology Corporation, Saitama (JP)

( * ) Notice: Subject to any disclaimer, the term of this patent is extended or adjusted under 35 U.S.C. 154(b) by 228 days.

(21) Appl. No.: 09/959,896

(22) PCT Filed: Mar. 13, 2001

(86) PCT No.: PCT/JP01/01972

§ 371 (c)(1),
(2), (4) Date: Dec. 12, 2001

(87) PCT Pub. No.: WO01/68254

PCT Pub. Date: Sep. 20, 2001

(65) Prior Publication Data

US 2004/0087437 A1 May 6, 2004

(30) Foreign Application Priority Data

Mar. 13, 2000 (JP) ........................................ 2000-069500

(51) Int. Cl.[7] .......................... B01J 31/00; B01J 23/00; C07C 49/00
(52) U.S. Cl. ..................... 502/152; 502/156; 502/308; 568/303; 568/383; 568/388; 568/406
(58) Field of Search ................................ 502/308, 152, 502/156; 568/303, 383, 388, 405, 406, 408, 417

(56) References Cited

FOREIGN PATENT DOCUMENTS

JP         2001-11006       1/2001

OTHER PUBLICATIONS

Nagayama, Journal of the American Chemistry Society, vol. 122, No. 46, pp. 11531–11532 (2000) (Nov.).

Kobayashi, Chemistry Letters, No. 1, pp. 71–72 (1999) (no month).

Primary Examiner—Michael LaVilla
(74) Attorney, Agent, or Firm—Wenderoth, Lind & Ponack, LLP

(57) ABSTRACT

A novel chiral lead catalyst comprising a lead compound of the following formula:

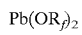

Pb(OR$_f$)$_2$ (wherein R$_f$ represents a fluorine-containing alkylsulfonyl group)

and a chiral crown ether compound having the structure of the following formula:

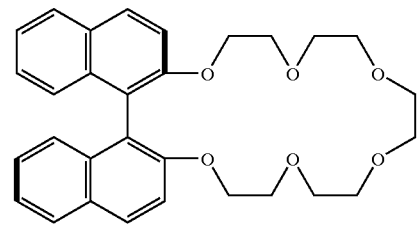

which is applicable in a variety of reactions, and enables simple reaction operations with high yield and high optical selectivity, is provided. Also provided is a method of asymmetric synthesis using the same.

5 Claims, No Drawings

CHIRAL LEAD CATALYST AND METHOD OF ASYMMETRIC ALDOL REACTION

TECHNICAL FIELD

The invention of the present application relates to a chiral lead catalyst and to a method of asymmetric aldol reaction. More precisely, the invention of the present application relates to a novel chiral lead catalyst that enables high yield and high optical selectivity and enables asymmetric synthesis in mild conditions, and to a method of using the said catalyst for asymmetric aldol reaction.

BACKGROUND ART

The realization of a method for asymmetric synthesis with high yield and good optical selectivity has become an important issue for chemical synthesis in such fields as medicine, fragrance and the like. In asymmetric synthesis, catalyst-assisted methods are especially attracting attention.

As such catalysts, those with chiral ligand compounds coordinated on metal elements have been proposed. However, such conventional chiral catalysts are limited in the type of reaction to which they are applicable, and often require strict reaction conditions such as, completely anhydrous conditions and extremely low temperatures, thereby restricting reaction conditions and operationality.

On the other hand, the inventors of the present application have found that certain metal compounds are stable in or in the presence of water and serve as Lewis acid catalysts, and that by using such compounds, basic and important carbon-carbon bond-forming organic synthesis reactions such as aldol reaction and Diels-Alder reaction proceed smoothly; based on such findings, the inventors have thus proposed novel catalyst systems.

Taking in consideration the above-mentioned inventors' knowledge and new proposals, the object of the present invention is to solve the problems of conventional asymmetric synthesis, and to provide a novel catalyst which is widely applicable and enables asymmetric synthesis with high yield and high optical selectivity under mild conditions even in the presence of water, and simplifies the reaction operation. Also, the object of the invention is to provide a method of asymmetric aldol reaction using this catalyst, which is basic and important for producing optically active β-hydroxycarbonyl compounds.

DISCLOSURE OF THE INVENTION

In order to solve the above-mentioned problems, the invention of the present application firstly provides a chiral lead catalyst comprising a lead compound of the following formula:

$$Pb(OR_f)_2$$

(wherein $R_f$ represents a fluorine-containing alkylsulfonyl group)
and a chiral crown ether compound having the structure of the following formula:

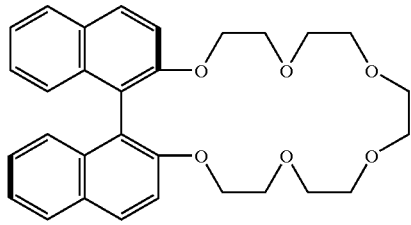

The invention of the present application secondly provides the chiral lead catalyst wherein the lead compound is a lead triflate; thirdly, the present invention provides the chiral lead catalyst wherein the binaphthyl ring of the chiral crown ether compound is substituted with hydrocarbon groups or halogen atoms.

Fourthly, the invention of the present application provides a method of asymmetric aldol reaction for the production of a hydroxyketone compound, comprising the reaction of an aldehyde reactant with a silyl enolether compound in the presence of the catalyst of any of the above first to third inventions, in an aqueous solvent. Fifthly, the invention provides the method of asymmetric aldol reaction wherein the aqueous solvent comprises water and alcohol.

BEST MODE FOR CARRYING OUT THE INVENTION

The invention of the present application is as described above; hereinafter, its embodiments are described in detail.

The lead compound that is the basic component of the chiral lead catalyst of the present invention is a fluorine-containing alkylsulfonate compound of lead. The fluoroalkyl group is an alkyl group wherein part or all of the hydrogen atoms are substituted with fluorine atoms. A preferred example of the perfluoroalkyl group is:

$$-SO_2-C_nF_{2n+1} \ (n \leq 10)$$

Among such perfluoroalkyl groups, a triflate group may be referred to as a typical example that may be used effectively in the present invention.

For the chiral crown ether compound, the binaphthyl ring may be substituted at the 6,6'-position with a substituent that does not interfere with the chiral catalyst activity, such as hydrocarbon groups, halogen atoms, alkoxy groups, and heterocyclic groups.

The hydrogen atoms constituting the oxyalkylene chain of the crown ether ring may also be substituted with desirable substituents.

The chiral lead catalyst of the present invention comprising the above-mentioned lead compound and chiral crown ether compound may be prepared by mixing the two constituent compounds in a solvent.

The solvent may be a polar solvent, including, for example, halogenated hydrocarbons, nitriles, sulfoxides and azides. For the preparation of the catalyst, the compounds may be mixed at a temperature in the range of, for example, about −10° C. to 10° C.

Regarding the amount of the lead compound and the chiral crown ether bis-compound to be used, for one mol of the lead compound, about 0.1 to 10 mols of the chiral crown ether compound may be added as the ligand. Also, for the preparation of the catalyst, if desired, any other ligand compound or reaction promoter may be added.

The thus-prepared chiral lead catalyst of the present invention shows Levis acidity, and enables the formation of carbon-carbon bond, which is a basic step in organic synthesis, while also enabling asymmetric synthesis even in the presence of water.

The invention of the present application provides as one specific mode of such asymmetric synthesis, the asymmetric aldol reaction. In other words, the present invention enables asymmetric synthesis of hydroxyketone compounds by the reaction of an aldehyde compound with a silyl enolether compound in an aqueous solvent in the presence of the above-described catalyst.

The asymmetric synthesis of hydroxyketone compounds may be represented, for example, by the following reaction scheme:

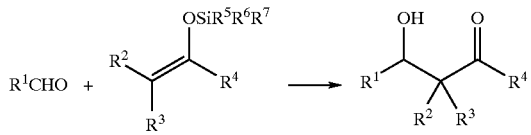

In the above scheme, $R^1$, $R^2$, $R^3$ and $R^4$ each represent a hydrocarbon group that may contain a substituent, or a hydrocarbon group that may contain a substituent, which is bonded to the compound via a hetero-atom such as oxygen or sulfur atom; $R^5$, $R^6$ and $R^7$ each represent a hydrocarbon group.

In the above reaction, an aqueous solvent is used. The aqueous solvent may be water, or a mixture of water and alcohol such as aliphatic or alicyclic alcohol, or a mixture of water and THF. The mixed solvent of water and alcohol is preferable in the invention. The ratio of water to alcohol is preferably less than or equal to 0.9 by volume.

Among them, branched alkyl alcohols such as isopropyl alcohol, isobutyl alcohol and tert-butyl alcohol may be used as effective in ensuring high reactivity and high selectivity.

Regarding the amount of the catalyst to be used in the reaction, the amount of the lead compound and the chiral crown ether compound may each be, for example, approximately 4 to 40 mol %. The ratio of the aldehyde compound to the silyl enolether compound used in the reaction may be, for example, approximately 1/10 to 10/1 by mol.

Regarding the reaction temperature, mild reaction conditions may be chosen. For example, the temperature may be in the range of −5° C. and 15° C.

The method of asymmetric aldol reaction of the present invention is advantageous in that the reaction operation is simple, and that the reaction temperature is mild, aqueous solvents favorable to the environment may be used, and extremely low temperature is not required. In addition, the yield and the asymmetric yield of the method are excellent.

Hereinafter, Examples are indicated to describe the invention of the present application in more detail.

It is needless to mention that the following Examples are not intended in any way to restrict the scope of the present invention.

EXAMPLES

Example 1

To a solution of Lead (II) triflate (0.1 mmol, 20 mol %), dried under argon at 100° C./1 mmHg for 1 hour, in methylene chloride (1 ml), a methylene chloride solution of the crown ether compound (0.12 mmols, 24 mol %) of the following formula:

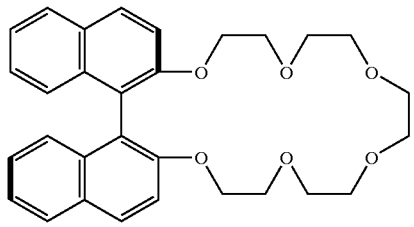

was added and stirred for 1 hour to prepare a chiral lead catalyst.

From the methylene chloride solution of the chiral lead catalyst thus prepared, the solvent was evaporated, then dissolved in $H_2O$-i-PrOH (1:4.5, 0.50 ml). After cooling at 0° C., $H_2O$:i-PrOH (1:4.5, 1.0 ml) solutions of benzaldehyde (0.5 mmols) and 1-phenyl-1-trimethylsiloxy-1-propene (0.75 mmols) were added consecutively. After stirring for 20 hours, ethyl acetate (15 ml) and aqueous saturated $NaHCO_3$ solution (10 ml) were added thereto to separate the organic layer, followed by the extraction of the product with ethyl acetate (10 ml×2). The resulting organic layer was dried over anhydrous sodium sulfate, then the solvent was evaporated away under reduced pressure, and the residue was purified through thin-layer silica gel chromatography to obtain 1,3-diphenyl-3-hydroxy-2-methyl-1-propanone (89%, syn:anti= 91:9, 69% ee (syn)).

The diastereomer ratio was determined by proton NMR. The optical purity of the syn-isomer was determined through HPLC analysis using an optical isomer separation column (Daicel Chemical industry's CHIRALPAK AD; hexane/2-propanol=30/1; retention time 17.88, 22.64 min (syn), 32.54, 36.54 min (anti)).

Example 2

The same asymmetric aldol reaction as in Example 1 was performed using various aldehyde compounds in place of benzaldehyde.

The results are given in Table 1.

TABLE 1

| Entry | Aldehyde Compound | Yield (%) | Syn/anti | ee % (syn) |
|---|---|---|---|---|
| 1 | (o-C)PhCHO | 74 | 82/18 | 62 |
| 2 | (o-Ome)PhCHO | 71 | 86/14 | 50 |
| 3 | Ph—CH=CH—CHO | 77 | 74/26 | 58 |
| 4 | 1-NapCHO | 63 | 90/10 | 44 |
| 5 | 2-NapCHO | 75 | 89/11 | 49 |
| 6 | $CH_3(CH_2)_2CHO$ | 45 | 90/10 | 60 |
| 7 | $CH_3(CH_2)_4CHO$ | 82 | 92/8 | 80 |
| 8 | $CH_3(CH_2)_7CHO$ | 79 | 90/10 | 82 |
| 9 | $Ph(CH_2)_2CHO$ | 60 | 88/12 | 76 |
| 10 | $(CH_3)_2CH(CH_2)_2CHO$ | 99 | 94/6 | 87 |
| 11 | $(CH_3)_2CHCH_2CHO$ | 65 | 90/10 | 78 |
| 12 | cyclohexyl-CHO | 75 | 89/11 | 73 |
| 13 | 2-thienyl-CHO | 87 | 90/10 | 75 |

In Entry 10, the reaction yield that gave the corresponding product, β-hydroxyketone compound is, indeed, 99%; and syn/anti=94/6, and syn=87% ee. For the other examples, the yield and the optical selectivity were high, as well.

Physical data by which the products were identified are shown below.

TABLE 2

3-Hydroxy-2-methyl-3-(1-naphtyl)-1-phenyl-1-propanone: (syn/anti = 90/10) syn:
$^1$HNMR (CDCl$_3$) δ 1.11(d.3HJ=7.3Hz), 3.83–3.89(m, 1H)4.01 (s, 1H), 5.98(s, 1H), 7.39–7.58(m 0.6H)7.72–7.89(m, 6H)
$^{13}$CNMR (CDCl$_3$) δ 11.3, 44.9, 69.2, 122.3, 124.4, 125.3, 125.4, 126.1, 127.8, 128.4, 128.5, 128.6, 128.8–129.2, 129.7. 133.69, 133.72, 135.6, 136.5, 206.4.
HPLC (Daicel Chiralcel AS, hexane/i-PrOH = 30/1, flow late = 1.0 mL/min). $^1$R = 23.20 min (minor). $^1$R = 29.34 min (major) (syn), HPLC (Daicel Chiralcel AD, hexane/i-PrOH = 30/1, flow late 1.0 mL/nin) $^1$R = 27.74 min (minor), $^1$R = 51.26 min (major) (anti).
3-Hydroxy-2-methyl-3-(2-naphtyl)-1-phenyl-1-propanone: (syn/anti = 89/11) syn:
$^1$HNMR (CDCl$_3$) δ 1.20(d, 3H. J=7.2Hz), 3.03(brs, 1H)3.80(dq.1H, J=2.9, 4.4Hz), 5.42(d. 1H, J=2.7Hz), 7.54–7.62(m, 6H), 7.81–8.02 (m, 6H).
$^{13}$CNMR (CDCl3) δ 15.8, 47.8. 76.9, 124.0, 125.9, 126.0, 126.2. 127.7, 128.0, 128.4, 128.6, 128.8. 133.11, 133.14, 133.3, 136.7, 139.5, 204.9.
anti:
$^1$HNMR (CDCl$_3$) δ 1.02(d, 3H, J=7.3Hz), 3.03(brs. 1H), 3.87(dq. 1H, J=7.4Hz), 5.09(d, 1H, J=7.8Hz), 7.38–7.52(m, 6H), 7.74–7.80(m, 46H), 7.92–7.94(m. 2H).
$^{13}$CNMR (CDCl$_3$) δ 11.2, 46.8, 73.1, 124.0, 124.9, 125.7. 126.0, 127.6, 127.9, 128.0, 128.4, 128.7, 132.7, 133.2, 133.5, 135.5, 139.2, 205.7.
HPLC (Daicel Chiralcel AD. hexane/iPrOH = 30/1, flow late = 1.0 mL/min). $^1$R = 32.19 min (minor). $^1$R = 36.06 min (major) (syn).
$^1$R = 32.51 min (mjnor), $^1$R = 36.16 min (major) (anti).

TABLE 3

3-Hydroxy-2-methyl-1-phenyl-1-hexanone: (syn/anti = 90/10)
syn:
1HNMR (CDCl3) δ 0.85–0.96(m, 4H). 1.20(d. 3H, J=7.0Hz), 1.28–1.61 (m3H), 3.38–3.4d(m. 1H)3.9714.01(m, 1H), 7.28–7.61(m. 3H). 7.88–7.91(m. 2H).
13CNMR(CDCl3)d11.0d. 14.03, 19.26, 36.45. 44.49, 71.02. 125.94. 128.43, 128.75, 133.41, 135.89, 205.93.
HPLC (Daicel Chiralcel AS. hexane/i-PrOH = 90/1, flow late = 1.0 mL/min), $^1$R: 16.10 min (minor), $^1$R = 26.82 min (major) (syn), $^1$R = 16.37 min (minor), $^1$R = 47.37 min (major) (anti).
3-Hydroxy-2-methyl-1-phenyl-1-octanone: (syn/anti = 92/8) syn:
$^1$H NMR (CDCl$_3$) δ 0.81–0.89(m, 3H). 1.19–1.60(m. 11H), 2.77(brs. 1H). 3.37–3.55(m. 1H). 3.95–4.00(m. 1H), 7.40–7.56(m, 3H), 7.88–7,92(m. 2H).
$^{13}$CNMR (CDCl$_3$) δ 10.6, 13.6. 22.2, 25.3, 31.4, 33.9, 44.1, 70.9, 127.9, 128.0, 128.3, 133.0, 135.5, 205.9.
HPLC (Daicel Chiralcel OD, hexane/iPrOH = 90/1, flow late = 1.0 mL/min). $^1$R = 11.18 min (minor). $^1$R = 16.62 min (major) (syn), $^1$R = 15.57 min (minor). $^1$R = 19.32 min (major) (anti).
3-Hydroxy-2-methyl-1-phenyl-1-undecanone: (syn/antj = 90/10) syn:
$^1$H NMR (CDCl$_3$) δ 0.80–0.85(m, 4H). 1.19–1.17(m, 16H), 3.08(brs. 1H), 3.38–3.45(m. 1H). 3.96–3.99(m. 1H). 7.41–7.45(m. 2H), 7.51–7.55(m, 1H). 7.88–7.91. (m, 2H).
$^{13}$CNMR (CDCl$_3$) δ 11.0. 14.0, 22.6. 26.1, 29.2, 29.5, 29.6, 31.8, 34.3, 34.8, 44.4, 71.3, 120.7, 1283, 133.4, 135.9, 205.9.
HPLC (Daicel Chiralcel AS. hexane/i-PrOH = 90/1. flow late = 1.0 mL/min). $^1$R = 10.52 min (minor), $^1$R = 15.11 min (major) (syn). $^1$R = 11.56 min (minor). $^1$R = 34.22 min (major) (anti).

TABLE 4

3-Hydroxy-2-methyl-1,5-diphenyl-4-pentene-1-one: (syn/anti = 88/12)
$^1$HNMR (CDCl$_3$) δ 1.23(d. 0.36H. J=7.2Hz), 1.30(d. 2.64H, J=73Hz), 3.10(brs. 1H)3.58–3.74(m. 1H), 4.59(ddd, 0.12H. J=0.7, 7.2. 7.2Hz), 4.76 (ddd, 0.88H, J=1.7, 3.9, 5.7Hz)6.23(dd, 0.88H, J=5.7, 15.8Hz), 6.28 (dd. 0.12H, J=7.2, 15.8Hz). 6.64(d, 0.12H, J=15.8Hz). 6.70(d. 0.88H, J=15.8Hz), 7.19–7.37(m, 5H). 7.42–7.48(m. 2H), 7.42–7.48(m. 2H), 7.53–7.59(m. 1H), 7.93–7.99(m. 2H).
$^{13}$CNMR (CDCl$_3$) δ 11.9, 15.2, 45.5, 46.3, 72.3, 75.1, 126.4, 126.5, 127.5, 127.7, 1283, 128.38, 128.42, 128.3, 128.6, 128.7, 129.2, 129.7, 130.9, 131.9, 133.3, 133.4, 135.8, 136.4, 136.5, 136.6, 204.6, 205.0.
HPLC (Daicel Chiralcel AS, hexane/iPrOH = 9/1. flow late = 1.0 mL/min). $^1$R = 9.39 min (minor). $^1$R = 13.59 min (major,) (syn). $^1$R = 10.26 min (minor), $^1$R = 21.76 min (major) (anti).
2,5-Dimethyl-3-hydroxy-1-phenyl-1-hexanone: (syn/anti. = 94/6) syn
$^1$H NMR (CDCl$_3$) δ 0.90–0.95(m. 6H). 1.26(d. 3H. J=73H=). 1.54–1.61 (m. 1H), 1.80–1.94(m, 1H), 3.39–3.45(m. 1H), 3.02(brs, 1H), 4.12–4.16 (m.. 1H), 7.46–7.54(m, 2H), 7.56–7.62(m. 1H), 7.94–7.97(m. 2H).
$^{13}$CNMR (CDCl$_3$) δ 11.1, 22.0, 23.5, 24.6, 43.4, 44.9, 128.4, 128.8, 133.4, 135.9, 206.0.
HPLC (Daicel Chiralcel AD. hexane/iPrOH = 200/1. flow late = 1.0 mL/min). $^1$R = 46.85 min (major), $^1$R = 95.00 min (major) (syn), $^1$R = 42.46 min (major), $^1$R = 56.03 min (major) (anti-).
3-Cyclohexyl-3-hydroxy-2-metyl-1-phenyl-1-propanone: (syn/anti = 82/18)
$^1$HNMR (CDCl$_3$) δ 1.17–1.88(m, 13H), 2.03(d, 0.82HJ=11.8Hz), 2.19(d, 0.18H, J=12.3Hz), 3.07–3.16(m, 1H), 3.62–3.85(m. 2H). 7.54–7.70(m. 3H), 8.00–8.06(m, 2H).
$^{13}$CNMR (CDCl$_3$) δ 10.5, 16.2, 25.8, 26.3, 26.1, 26.3, 26.4, 27.7, 29.15, 29.23, 29.4, 30.2, 40.2, 41.3, 41.8, 75.4, 78.9, 128.3, 128.39, 128.41, 128.74, 133.3, 133.4, 135.9, 136.6, 205.9, 206.4.
IR (neat) 3442, 1704 cm$^{-1}$.
HPLC (Daicel Chiralcel AS. hexane/iPrOH = 30/1. flow late = 1.0 mL/min). $^1$R = 7.74 min (minor). $^1$R = 13.86 min (major) (syn), $^1$R = 6.90 min (minor). $^1$R = 15.56 min (major) (anti).

Example 3

In place of 1-phenyl-1-trimethylsiloxy-1-propene, 1-(4-methoxyphenyl)-1-trimethylsiloxy-1-propene was reacted in the same manner as in Example 1. As a result, the reaction yield was 85%; and syn/anti=85/15, and syn=58% ee.

Example 4

The same reaction as in Example 1 was performed except that the ratio of H$_2$O:i-PrOH=1:4.5 (1.5 ml) in Example 1 was varied to 1:9.

As a result, the reaction yield was 92%; and syn/anti=91/9, and syn=62% ee.

Example 5

The same reaction as in Example 1 was performed using various aqueous alcohol solvents. The results are given in the following Table.

TABLE 5

| Solvent | Yield (%) | syn/anti | ee (%) (syn/anti/) |
|---|---|---|---|
| H$_2$O/EtOH = 1/9 | 62 | 90:10 | 55/6 |
| H$_2$O/THF = 1/9 | 97 | 90:10 | 36/6 |
| H$_2$O/MeOH = 1/9 | 62 | 84:16 | 46/3 |
| H$_2$O/BuOH = 1/9 | 76 | 89:11 | 62/11 |
| H$_2$O/PrOH = 1/9 | 92 | 91:9 | 62/10 |
| H$_2$O/BuOH = 1/9 | 62 | 91:9 | 55/4 |

Example 6

Using different chiral crown ether compounds, the same reaction as in Example 4 was performed. The results are given in Table 6.

TABLE 6

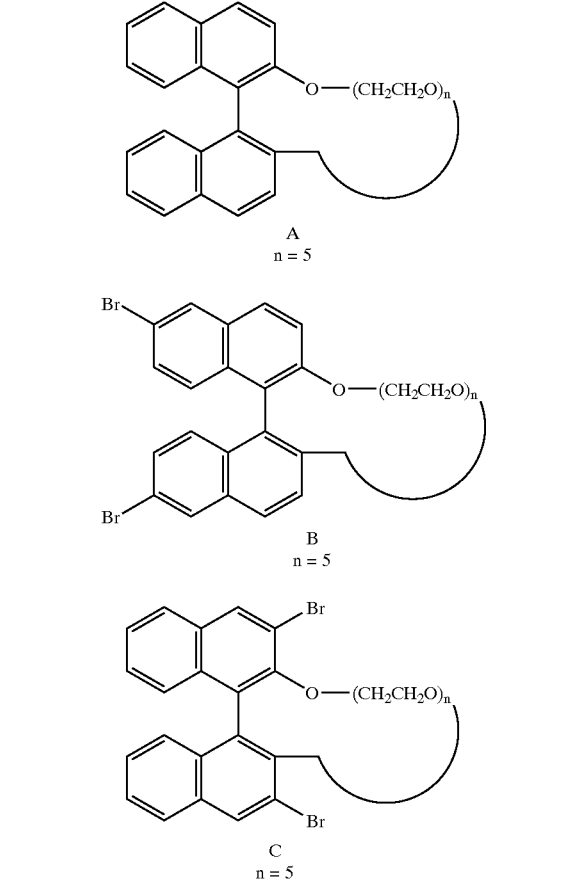

A
n = 5

B
n = 5

C
n = 5

TABLE 6-continued

[Structure D: binaphthyl with Br substituent, O—(CH$_2$CH$_2$O)$_n$ linker]
D
n = 5

[Structure E: binaphthyl with Me substituents, O—(CH$_2$CH$_2$O)$_n$ linker]
E
n = 5

[Structure F: binaphthyl with Ph substituents, O—(CH$_2$CH$_2$O)$_n$ linker]
F
n = 5

| Entry | Ligand | MXn | Yield (%) | syn/anti | ee (%) (syn/anti) |
|---|---|---|---|---|---|
| 1 | A | Pb(OTf)$_2$ | 92 | 91:9 | 62/10 |
| 2 | B | Pb(OTf)$_2$ | 92 | 90:10 | 61/5 |
| 3 | C | Pb(OTf)$_2$ | 100 | 86:14 | 43/28 |
| 4 | D | Pb(OTf)$_2$ | 90 | 86:14 | 38/8 |
| 5 | E | Pb(OTf)$_2$ | 95 | 81:19 | 35/7 |
| 6 | F | Pb(OTf)$_2$ | 97 | 88:12 | 17/12 |

INDUSTRIAL APPLICABILITY

As described in detail above, by the invention of the present application, a novel catalyst of wide use, which enables simple and mild reaction and realizes high yield and high optical selectivity, as well as a method of using the catalyst for asymmetric synthesis, is provided.

What is claimed is:

1. A chiral lead catalyst comprising a lead compound of the following formula:

Pb(OR$_f$)$_2$ wherein R$_f$ represents a fluorine-containing alkylsulfonyl group and a chiral crown ether compound having the structure of the following formula:

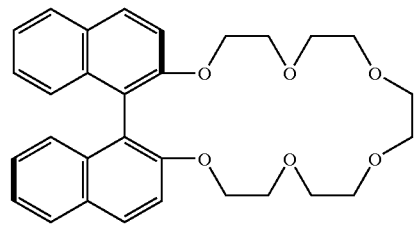

and wherein the chiral crown ether compound is coordinated with the lead compound.

2. The chiral lead catalyst of claim 1, wherein the lead compound is a lead triflate.

3. The chiral lead catalyst of claim 1, wherein the binaphthyl ring of the chiral crown ether compound is substituted with hydrocarbon groups or halogen atoms.

4. A method of asymmetric aldol reaction for the production of a hydroxyketone compound, comprising the reaction of an aldehyde reactant with a silyl enolether compound in the presence of the catalyst of claim 1, in an aqueous solvent.

5. The method of asymmetric aldol reaction of claim 4, wherein the aqueous solvent comprises water and alcohol.

* * * * *

UNITED STATES PATENT AND TRADEMARK OFFICE
CERTIFICATE OF CORRECTION

PATENT NO. : 6,780,812 B2
DATED : August 24, 2004
INVENTOR(S) : Shu Kobayashi

It is certified that error appears in the above-identified patent and that said Letters Patent is hereby corrected as shown below:

Title page,
Item [75], Inventors, "Saitama" should read -- Tokyo --.

Signed and Sealed this

Seventh Day of December, 2004

JON W. DUDAS
*Director of the United States Patent and Trademark Office*